(12) United States Patent
Sato (10) Patent No.: US 7,809,429 B2
(45) Date of Patent: Oct. 5, 2010

(54) IMAGING APPARATUS

(75) Inventor: Hideo Sato, Tokyo (JP)

(73) Assignee: Sony Corporation, Tokyo (JP)

( * ) Notice: Subject to any disclaimer, the term of this patent is extended or adjusted under 35 U.S.C. 154(b) by 1694 days.

(21) Appl. No.: 11/010,292

(22) Filed: Dec. 14, 2004

(65) Prior Publication Data

US 2005/0143652 A1 Jun. 30, 2005

(30) Foreign Application Priority Data

Dec. 24, 2003 (JP) ............................. 2003-428405

(51) Int. Cl.
*A61B 6/00* (2006.01)
*G02F 1/01* (2006.01)
(52) U.S. Cl. .................. 600/473; 600/476; 250/330
(58) Field of Classification Search .............. 600/473, 600/476; 250/330
See application file for complete search history.

(56) References Cited

U.S. PATENT DOCUMENTS

2002/0067419 A1* 6/2002 Inoue et al. ............ 348/333.03
2002/0183624 A1* 12/2002 Rowe et al. ................. 600/476
2005/0285038 A1* 12/2005 Frangioni .................... 250/330

FOREIGN PATENT DOCUMENTS

| JP | 7-246185 | 9/1995 |
|---|---|---|
| JP | 2002-42117 | 2/2002 |
| JP | 2002-142228 | 5/2002 |
| JP | 2004-86412 | 3/2004 |

OTHER PUBLICATIONS

U.S. Appl. No. 10/546,038, Aug. 17, 2005, Sato.

* cited by examiner

*Primary Examiner*—Eric F Winakur
*Assistant Examiner*—Katherine L Fernandez
(74) *Attorney, Agent, or Firm*—Oblon, Spivak, McClelland, Maier & Neustadt, L.L.P.

(57) ABSTRACT

To improve usability. This invention provides an imaging apparatus that operates in a first mode to image a subject as an imaging target and in a second mode to image an inside of a body as an imaging target. This imaging apparatus comprises: an irradiation means for irradiating a body with near-infrared light of a prescribed luminance level; a filter means comprising a color filter array with color pixels for performing color dispersion on visible light reflected by a subject and a near-infrared light pixel for allowing near-infrared light to pass therethrough as a unit; and an exposure time adjustment means for adjusting exposure time of a solid imaging element for performing photoelectric conversion on dispersed light and pattern near-infrared light.

16 Claims, 11 Drawing Sheets

IMAGING APPARATUS

BACKGROUND OF THE INVENTION

1. Field of the Invention

This invention relates to an imaging apparatus and, more particularly, is suitably applied to a case of imaging blood vessel tissues existing inside a body, for example.

2. Description of the Related Art

As a target of biometrics identification, a unique body maker such as irises or fingerprints of a finger or a palm is used.

Recently, a formation pattern of blood vessel tissues existing inside a body is targeted as one of such body markers. An imaging apparatus for imaging a formation pattern of blood vessels has been proposed with using such a feature that light (near-infrared light) of near-infrared light bandwidth is specifically absorbed in deoxygenization hemoglobin (venous blood) or oxygenation hemoglobin (arterial blood) in blood vessels (for example, refer to "Weekly Bio" 49th edition, venous blood matching apparatus, [online], [search on Jan. 24, 2003], Internet <URL:http//www.mackport.co.jp/WEEKLY-BIO/bio49/bio.049.htm>).

Figure 1:
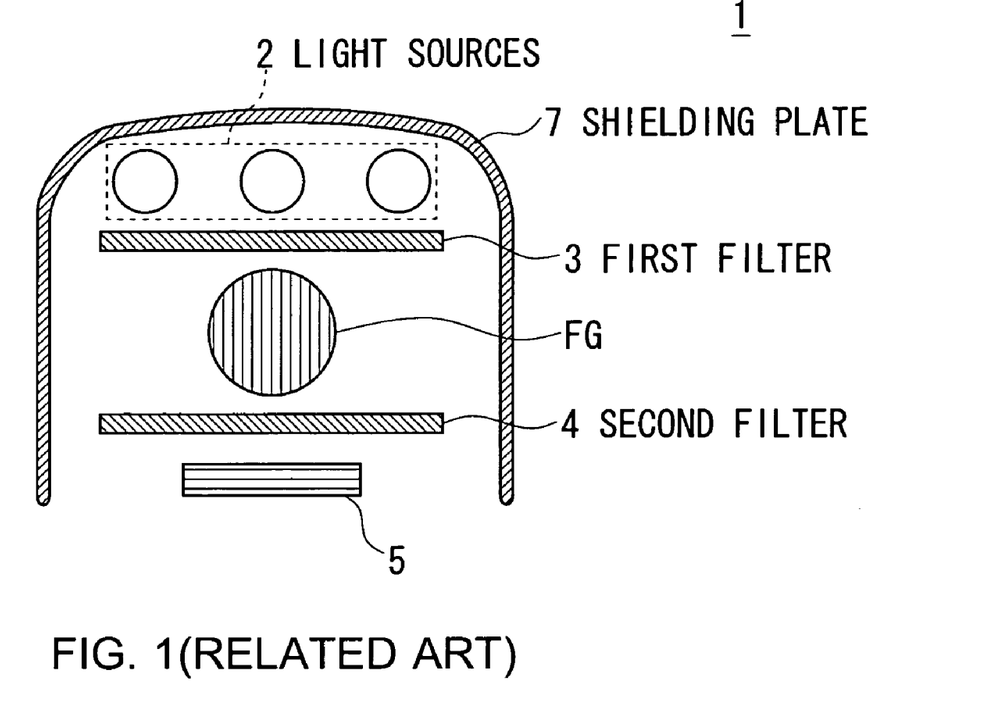
FIG. 1 is a schematic diagram showing a construction of a conventional imaging apparatus.

FIG. 1 schematically shows a blood vessel imaging apparatus 1. This blood vessel imaging apparatus 1 has laser light sources 2 for emitting near-infrared light. On a light path of the near-infrared light to be emitted from the laser light sources 2, a first filter 3 for allowing specific light of near-infrared light bandwidth out of the near-infrared light to pass therethrough, a second filter 4 for allowing light of near-infrared light bandwidth which is absorbed in hemoglobin in blood vessels, out of the light obtained through the first filter 3, and an imaging element 5 are arranged in order.

In the blood vessel imaging apparatus 1, the light sources 2 irradiate a human finger FG with near-infrared light via the first filter 3, the finger FG being inserted between the first filter 3 and the second filter 4. This near-infrared light is specifically absorbed in intrinsic hemoglobin in the blood vessels of the finger FG, and passes therethrough or is reflected by the other tissues, so that the near-infrared light obtained through the finger FG enters the imaging element 5 via the second filter 4 as blood vessel pattern light representing the formation pattern of the blood vessel tissues.

Then the imaging element 5 performs photoelectric conversion with a plurality of photoelectric conversion elements which are arranged in a reticular pattern so as to correspond to pixels, thereby creating a blood vessel image signal.

However, in an imaging apparatus with both a blood vessel imaging function to image blood vessel tissues of a body as an imaging target, like the above imaging apparatus 1, and a normal imaging function to image a subject such as background or a body, as an imaging target, like a general imaging apparatus, a complicated optical system should be adopted in order to image both near-infrared light which is used for imaging blood vessels and visible light obtained in normal imaging without deteriorating image quality.

One technique to simply solve the above problem is to mechanically arrange a filter for allowing only near-infrared light to pass therethrough in imaging blood vessels, at a prescribed position of an optical system. In this case, such a specially arranged filter increases a circuit scale, which does not meet a portability request. In addition, mechanical switching makes the usage complicated and looses comfort, resulting in deteriorating usability.

SUMMARY OF THE INVENTION

This invention has been made in view of foregoing and proposes an imaging apparatus capable of improving usability.

To solve the above problems, this invention provides an imaging apparatus that operates in a first mode to image a subject as an imaging target and in a second mode to image an inside of a body as an imaging target. This imaging apparatus comprises: an irradiation means for irradiating a body with near-infrared light of a prescribed luminance level; a filter means comprising a color filter array with prescribed color pixels for performing color dispersion on visible light reflected by the subject and a near-infrared light pixel for allowing near-infrared light to pass therethrough as a unit; and an exposure time adjustment means for adjusting exposure time of a solid imaging element for performing photoelectric conversion on dispersed light and pattern near-infrared light.

Further, this invention provides an imaging apparatus that operates in a first mode to image a subject as an imaging target and in a second mode to image an inside of a body as an imaging target. This imaging apparatus comprises: an irradiation means for irradiating a body with near-infrared light of a prescribed luminance level; a filter means for allowing visible light reflected by a subject and near-infrared light to pass therethrough; an exposure time adjustment means for adjusting exposure time of a solid imaging element for performing photoelectric conversion on visible light and near-infrared light; and a signal processing means for performing a prescribed signal process on a result of the photoelectric conversion of the solid imaging element. The filter means comprises a color filter array with a plurality of color pixels for performing color dispersion on visible light as a unit, and a relative near-infrared-light transparent ratio of the color pixels is selected so that near-infrared light components included in a signal subjected to the signal process have a prescribed value or lower.

According to this invention, both imaging targets can be imaged with one filter means and solid imaging element, which realizes downsizing. In addition, as compared with a case of providing special filters corresponding to modes, complexity in manufacturing and usage can be eliminated, resulting in improving usability.

The nature, principle and utility of the invention will become more apparent from the following detailed description when read in conjunction with the accompanying drawings in which like parts are designated by like reference numerals or characters.

DETAILED DESCRIPTION OF THE EMBODIMENT

Preferred embodiments of this invention will be described with reference to the accompanying drawings:

(1) First Embodiment

(1-1) Construction of Imaging Apparatus

Figure 2:
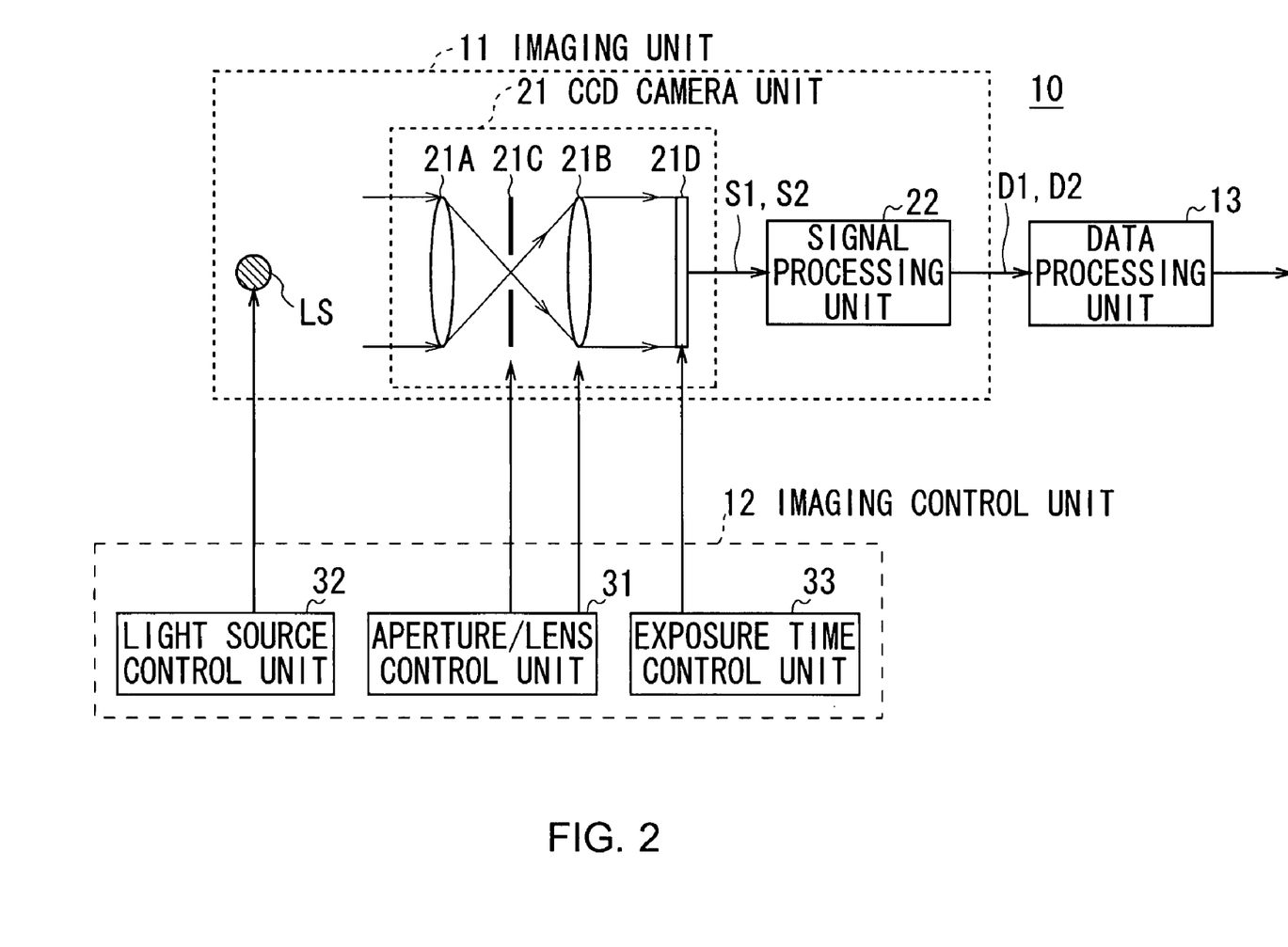
FIG. 2 is a schematic diagram showing a construction of an imaging apparatus according to the first embodiment.

FIG. 2 shows an imaging apparatus 10 according to this embodiment. This imaging apparatus 10 is composed of an imaging unit 11, an imaging control unit 12 and a data processing unit 13, and executes a first mode (hereinafter, referred to as normal imaging mode) to image a subject such as a body or background as an imaging target.

In this case, the imaging unit 11 guides reflected light (visible light) coming from a subject existing in front of a CCD camera unit 21, to a color CCD 21D via a lens 21A, an aperture 21C, and a lens 21B.

At this time, an aperture/lens control unit 31 of the imaging control unit 12 adjusts the amount of the visible light which enters the color CCD 21D, with automatic exposure control to control the aperture value of the aperture 21C, and also adjusts a focus distance and focus position to the imaging target, with auto focus control to control the positions of the lens 21A and 21B.

An exposure time control unit 33 adjusts the exposure time of the color CCD 21D by supplying a readout clock specifying exposure time of the color CCD 21D.

In such conditions, the color CCD 21D performs the photoelectric conversion on visible light arriving via the lens 21B, with photoelectric conversion elements arranged in a matrix, reads a charge signal which has been stored in each photoelectric conversion element through the photoelectric conversion, as a subject image signal S1 according to the readout clock, and sends it to a signal processing unit 22.

The signal processing unit 22 performs a prescribed signal process and then analog/digital (A/D) conversion on the image signal S1, and sends the resultant subject image data D1 to the data processing unit 13.

The data processing unit 13 performs a prescribed data process on the subject image data D1 and stores and keeps the resultant in, for example, an internal memory (not shown).

The imaging apparatus 10 executes the normal imaging mode as described above, to image a subject such as a body or background as an imaging target.

In addition to the above units, near-infrared light sources LS (LSa and LSb) for emitting near-infrared light to a direction opposite the outside light in the air arriving at the CCD camera unit 21 are arranged at the almost same level as the CCD camera unit 21, so that the imaging apparatus 10 can execute a mode (hereinafter, referred to as blood vessel imaging mode) to image the blood vessel tissues inside a finger FG positioned in an irradiation direction on the camera unit 21 as an imaging target (hereinafter, referred to as in-body imaging target).

In this case, when prescribed blood vessel imaging is requested with an operating unit (not shown), the imaging control unit 12 (FIG. 2) starts the light source control unit 32 in addition to the aperture/lens control unit 31.

The light source control unit 32 performs light source control to control an output value such as voltage to be output to the near-infrared light sources LS so as to have a prescribed value as a luminance level higher than that of the outside light normally obtained in the air, thereby irradiating the finger FG with near-infrared light of the luminance level higher than the outside light.

Figure 3:
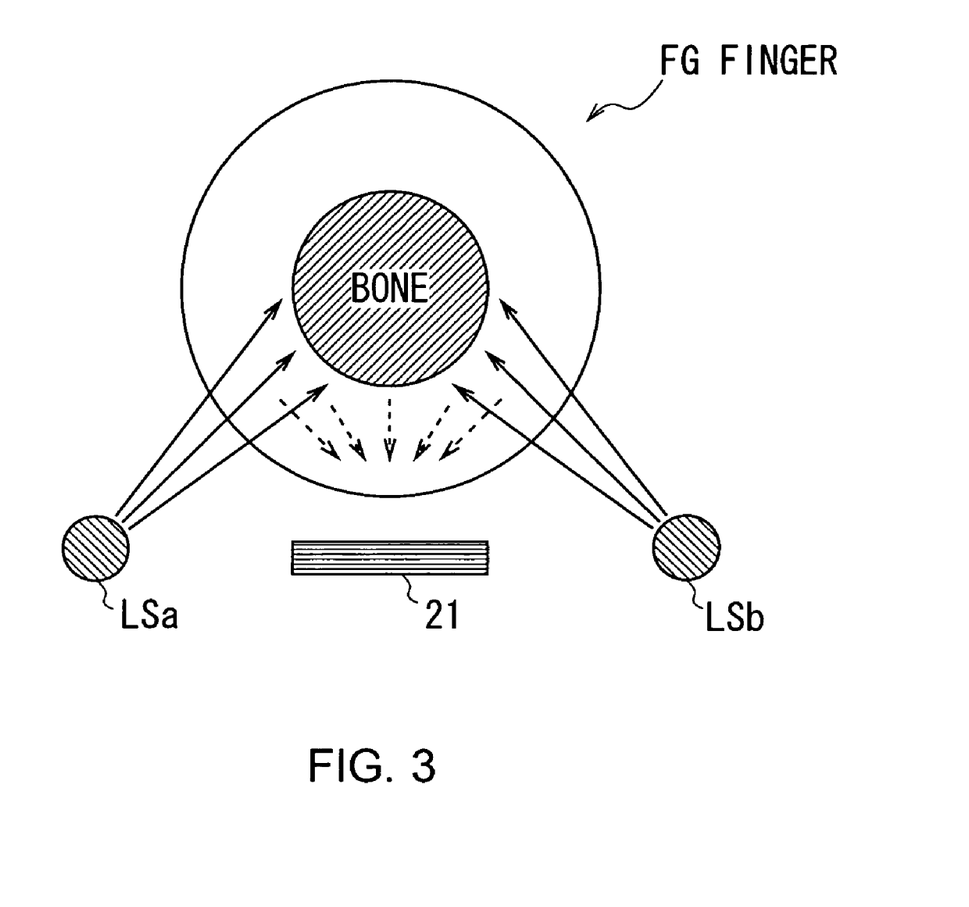
FIG. 3 is a schematic diagram showing an arrangement of near-infrared light sources and a flow of near-infrared light.

As shown in FIG. 3, the near-infrared light is specifically absorbed in intrinsic hemoglobin in blood vessel tissues (not shown) in the finger FG, and passes through or is reflected by the other tissues. The outside light arriving at this time, on the other hand, is attenuated by bones and so on and becomes light which can be ignored because of the stronger near-infrared light. Therefore, near-infrared light obtained via the finger FG enters the color CCD 21D via the lens 21A, the aperture 21C, the lens 21B and the RGB filter 21D as shown in FIG. 2 in order, as blood vessel pattern light representing a formation pattern of the blood vessel tissues.

Each photoelectric conversion element of the color CCD 21D stores a charge signal obtained as a result of the photoelectric conversion of the arriving blood vessel pattern light.

At this time, the exposure time control unit 33 adjusts the imaging sensitivity of the color CCD 21D to the blood vessel pattern light with exposure time control (electronic shutter) to electrically limit the amount of a charge signal stored in each photoelectric conversion element of the color CCD 21D.

Figure 4A:
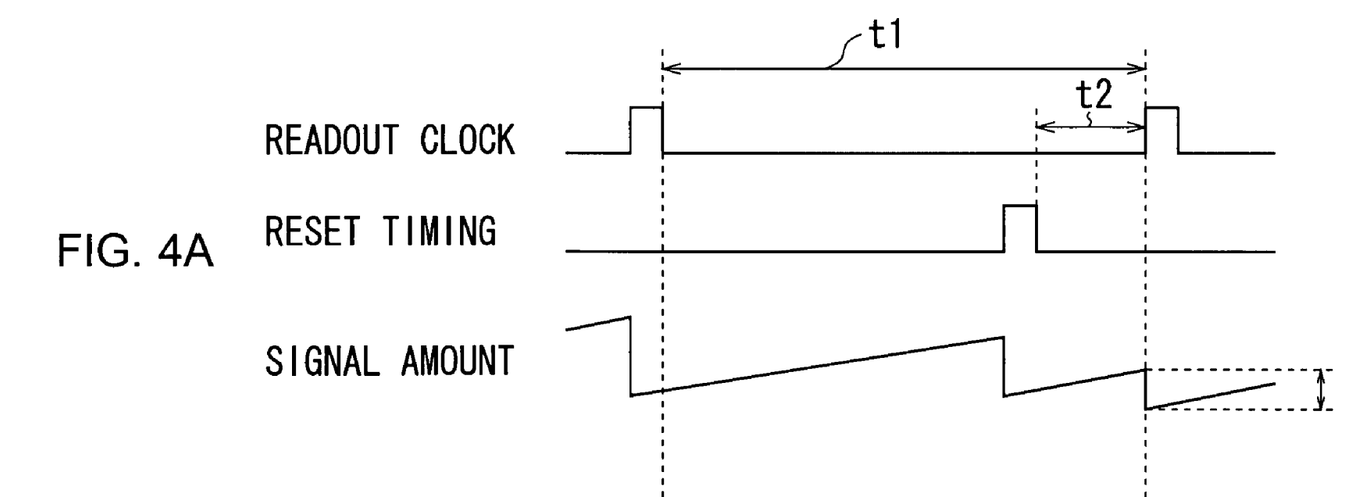
FIGS. 4A and 4B are schematic diagrams explaining electronic shutter.
Figure 4B:
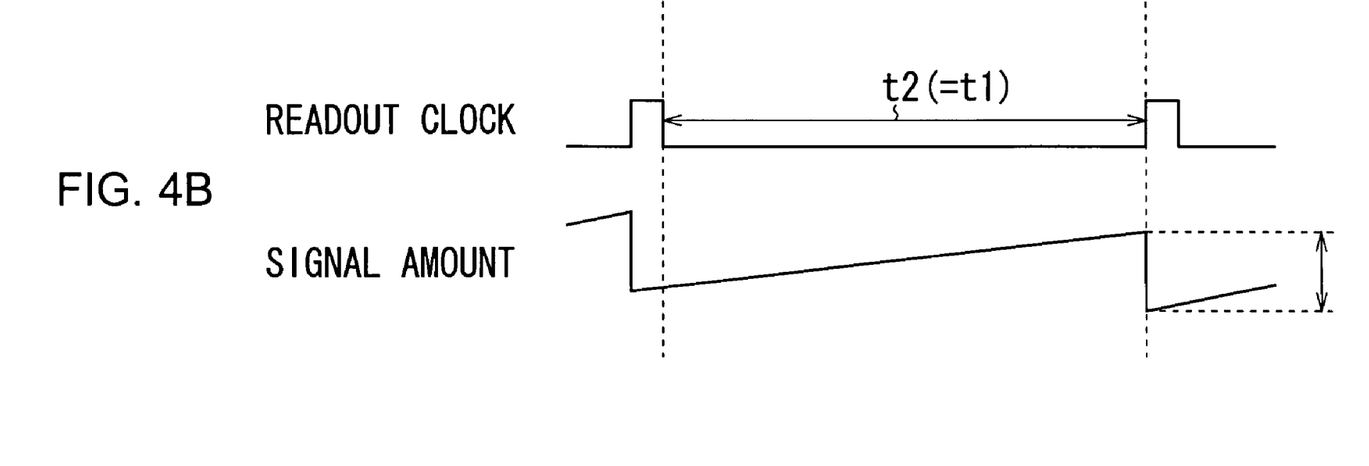

Specifically, as shown in FIGS. 4A and 4B, the exposure time control unit 33 variably controls prescribed reset timing within a charge storage period t1 from falling of a readout clock till rising which is the next readout timing. By making a period (hereinafter, referred to as exposure period) t2 (FIG. 4A) from the reset timing till the readout timing shorter than that of the normal imaging mode (FIG. 4B), the exposure time control unit 33 sets the reset timing so that the imaging sensitivity of the solid imaging element 21E to the blood vessel pattern light becomes optimal.

Figure 5A:
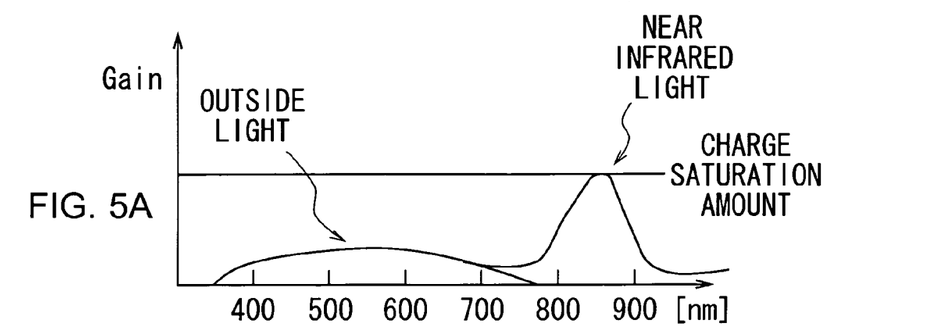
FIGS. 5A and 5B are schematic diagrams explaining adjustment of imaging sensitivity by the electronic shutter.
Figure 5B:
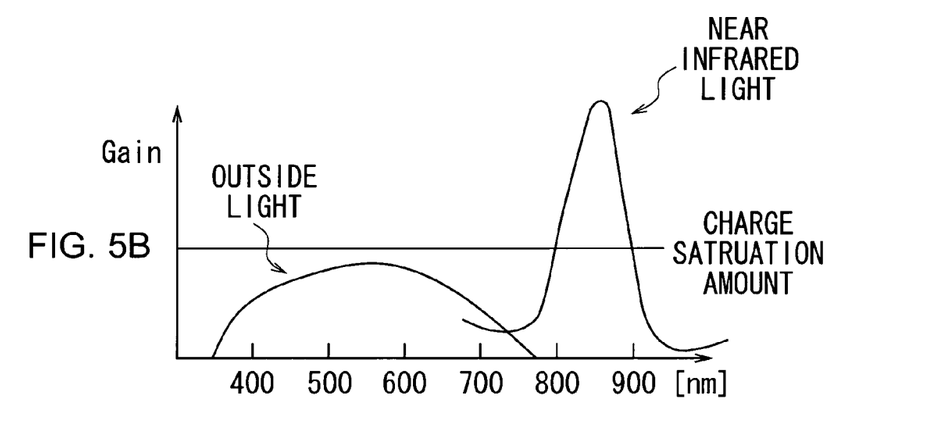

In this case, as shown in FIG. 5A, because the luminance level of near-infrared light emitted from the near-infrared light sources LS is higher than that of the outside light, the imaging sensitivity control unit 33 can previously prevent the charge signals stored in the photoelectric elements from being saturated within the charge storage period t1 (FIG. 5). In addition, as shown in FIG. 5B, the imaging sensitivity control unit 33 can relatively reduce the amount of the charge signals which are stored in the photoelectric elements as a result of performing the photoelectric conversion on the blood vessel pattern light and the outside light arriving at this time, so as to deteriorate only the imaging sensitivity of the solid imaging element 21E to the outside light.

Therefore, the color CCD 21D can read the charge signals which were limited through the exposure time control of the exposure time control unit 33, as a blood vessel image signal S2 (FIG. 2) representing the blood vessel tissues of the finger FG without influences of the outside light, and gives this blood vessel image signal S2 via the signal processing unit 22 to the data processing unit 13 as blood vessel image data D2.

The data processing unit 13 extracts the blood vessel formation pattern from the blood vessel image of the blood vessel image data D2, and stores and keeps the extracted unique blood vessel formation pattern in an internal memory (not shown) as identification information with high confidentiality, as compared with a case of extracting a pattern of fingerprints existing on a body.

The imaging apparatus 10 executes the blood vessel imaging mode as described above to image blood vessel tissues in the finger FG of the body.

This imaging apparatus 10 can image both a normal subject and blood vessel tissues of a body as described above, thus improving usability because different imaging apparatuses are not required for imaging subjects.

Note that the imaging apparatus 10 irradiates the finger FG with light of wavelength which is specifically absorbed in both oxygenation hemoglobin and deoxygenization hemoglobin out of hemoglobin (transport protein) of blood vessel tissues of the finger FG, that is, near-infrared light of 700 nm to 900 nm wavelength.

Thereby the imaging apparatus 10 can create a digital blood vessel image signal S2 faithfully representing the capillary tissues containing oxygenation and deoxygenization hemoglobin, with the CCD camera unit 21. As a result, since a blood vessel formation pattern can be correctly extracted, identification information with higher confidentiality can be created.

Further, in this case, as compared with a case of irradiating the finger FG with near-infrared light of which the wavelength is strictly limited to a wavelength which is specifically absorbed in oxygenation and deoxygenization hemoglobin, an S/N ratio of the CCD camera unit 21 can be made lower, and hemoglobin can be prevented from varying due to concentration of energy to the blood vessel tissues.

(1-2) Construction of Color CCD

Figure 6:
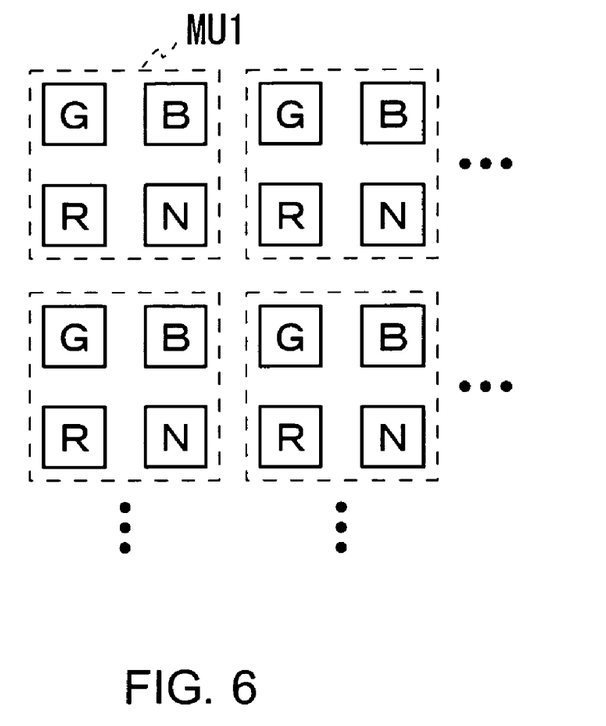
FIG. 6 is a schematic diagram showing a color filter array of an RGB filter.

The color CCD 21D has a color filter matrix array with four neighboring color pixels as one unit (hereinafter, referred to as a unit for signal processing). Specifically, as shown in FIG. 6, the color CCD 21D has a color filter array with color pixels "R", "G" and "B", and a pixel "N" for allowing near-infrared light of prescribed bandwidth to pass therethrough, as a unit for signal processing MU1. That is, as compared with general color CCDs which have color pixels "R", "G", "G", "B" as a unit for signal processing, this color CCD 21D has a different feature in that an "N" pixel is provided instead of two "G" pixels.

In addition, "N" pixels of this color CCD 21D have such color filter characteristics as to allow only near-infrared light of wavelengths from 700 nm to 900 nm obtained via a finger FG from the near-infrared light sources LS to pass therethrough.

In this case, as to signals output from the color CCD 21D, the signal processing unit 22 performs a signal process on signals from the color pixels "R", "G" and "B" as a subject image signal S1 in the normal imaging mode, or performs a signal process on signal from the pixels "N" as a blood vessel image signal S2 in the blood vessel imaging mode.

Therefore, the imaging apparatus 10 does not require a special filter for allowing only near-infrared light to pass therethrough in imaging blood vessels, thereby eliminating complexity in usage in switching to such a special filter. In addition, the imaging apparatus 10 can use the CCD camera unit 21 and the signal processing unit 22 for imaging both a normal subject and blood vessel tissues inside a body, thereby realizing downsizing.

(1-3) Operation and Effects of the First Embodiment

In the above configuration, this imaging apparatus 10 irradiates a body with near-infrared light of a higher luminance level than light in the air and adjusts exposure time of the color CCD 21D for performing the photoelectric conversion on blood vessel pattern light obtained via the body.

The imaging apparatus 10 images both a subject and blood vessel tissues with the color CCD 21D comprising a color filter array with color pixels "R", "G" and "B" for performing color dispersion on visible light reflected by the subject in the normal imaging mode and a pixel "N" (near-infrared light pixel) for allowing blood vessel pattern light (near-infrared light) obtained via the body to pass therethrough in imaging blood vessels, as a unit.

Therefore, the imaging apparatus 10 does not require a special filter for allowing only near-infrared light to pass therethrough in imaging blood vessels, resulting in eliminating complexity in usage in switching to such a special filter. In addition, the imaging apparatus 10 can use the CCD camera unit 21 and the signal processing unit 22 for imaging both a normal subject and blood vessel tissues inside a body, resulting in realizing downsizing.

According to the above configuration, both imaging targets can be imaged with one color CCD 21D, which realizes downsizing and also eliminates complexity in manufacturing and usage, as compared with a case of providing special filters corresponding to modes, resulting in improving usability.

(1-4) Other Configurations in the First Embodiment

The above first embodiment has described a case of applying the color CCD 21D (that is, integrated with the CCD) as a filter means comprising a color filter array with prescribed color pixels for performing color dispersion on visible light reflected by a subject and a near-infrared light pixel for allowing near-infrared light to pass therethrough. This invention, however, is not limited to this and a filter comprising the color filter array of the color CCD 21D can be provided at a prescribed position on the light path, differently from the CCD.

Further, the above first embodiment has described a case of using the color CCD 21D (FIG. 6) comprising a color filter array with four color pixels "R", "G", "B", and "N" as the unit for signal processing MU1. This invention, however, is not limited to this and a color CCD comprising a color filter array with five color pixels "R", "G", "B", "N", and "G" as a unit for signal processing can be used. In this case, the entrance area of light is enlarged by physically increasing the number of "G" pixels which have high sensitivity to visual light, so that a subject image signal can be obtained without loosing color purity balance in the normal mode, resulting in improving image quality of the subject image.

Furthermore, the above first embodiment has described a case of using the color CCD 21D (FIG. 6) comprising a color filter array with four color pixels "R", "G", "B", and "N" as the unit for signal processing MU1. This invention, however, is not limited to this and a color CCD that comprises the color filter array and adopts an all-pixel readout method can be used. In this case, the same effects as above embodiment can be obtained.

Figure 7:
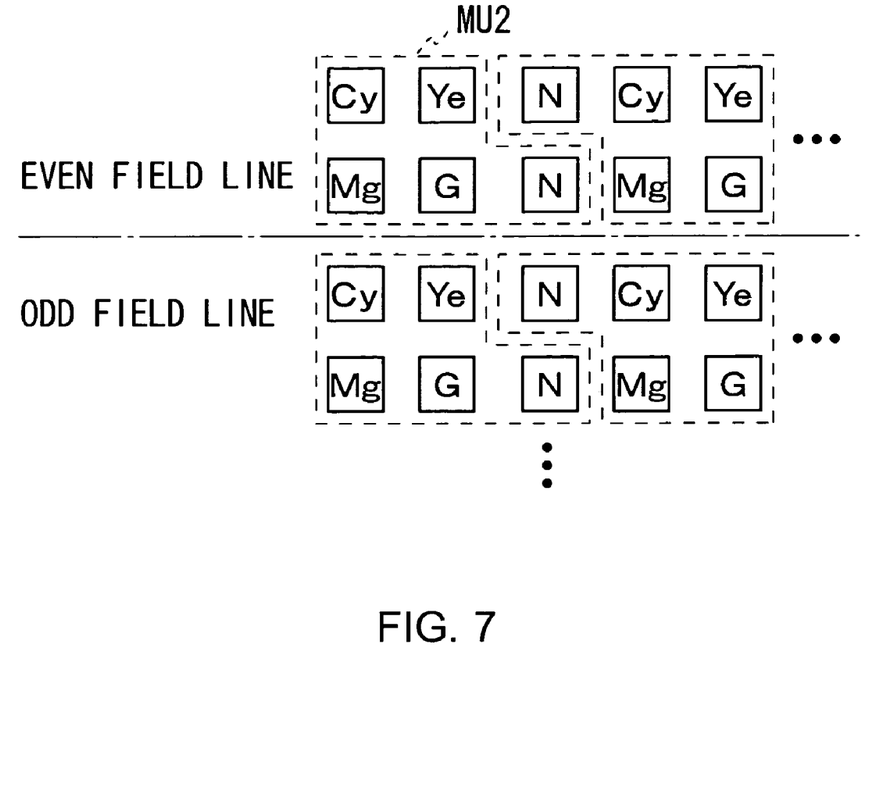
FIG. 7 is a schematic diagram showing a color filter array of a complementary color filter.

Furthermore, the above first embodiment has described a case of using the RGB color CCD 21D. This invention, however, is not limited to this and, as shown in FIG. 7, a complementary color CCD comprising a color filter array with color pixels "Cy", "Mg", "Ye", "G", and "N" as a unit for signal processing MU2 can be used.

Figure 8:
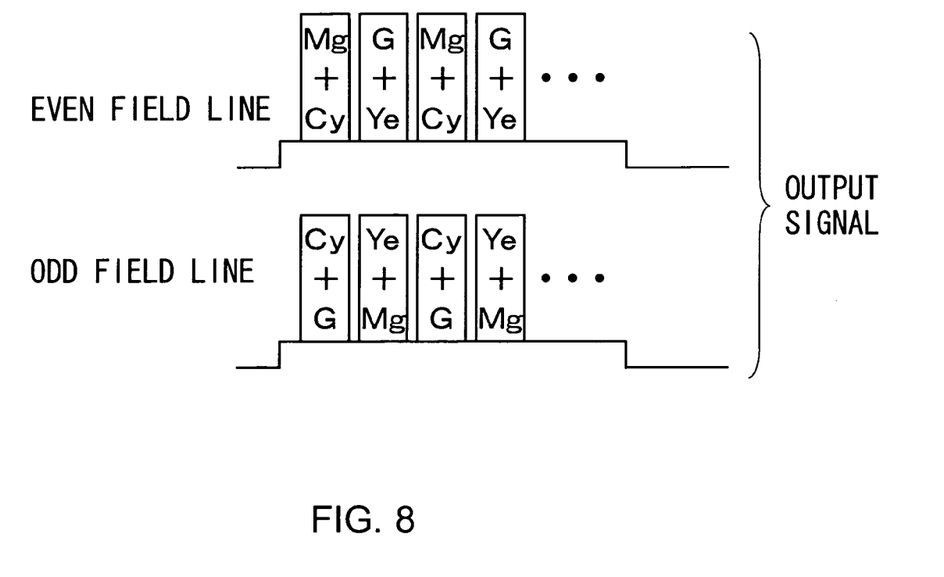
FIG. 8 is a schematic diagram explaining an output signal in a complementary checker color difference line sequential method.

In a case of a color CCD adopting the all-pixel readout method as the complementary color CCD, the positions of the "N" pixels are not necessarily limited. In a case of adopting the complementary checker color difference line sequential method, signals output from the complementary system color CCD are not output as independent signals corresponding to color pixels but are sequentially output as composite signals each from two pixels in a column for every odd or even field line, as shown in FIG. 8. Therefore, as shown in FIG. 7, the "N" pixels neighboring each other on an even (odd) field should be arranged on the same column, each "N" pixel being part of the unit for signal processing MU2.

By adopting a complementary system color CCD which emphasizes sensitivity and imaging more than color difference as described above, a moving subject can be imaged more effectively, as compared with the first embodiment.

Furthermore, the above first embodiment has described a case of using the color CCD 21 as a solid imaging element. This invention, however, is not limited to this and a Complementary Metal Oxide Semiconductor (CMOS) can be used instead.

In this case, differently from the CCD, the CMOS can easily obtain a pixel-independent signal by controlling horizontal and/or vertical scanning. Therefore, the same effects as the above embodiment can be obtained without limiting arrangement conditions.

(2) Second Embodiment (2-1) Construction of Imaging Apparatus

Figure 9:
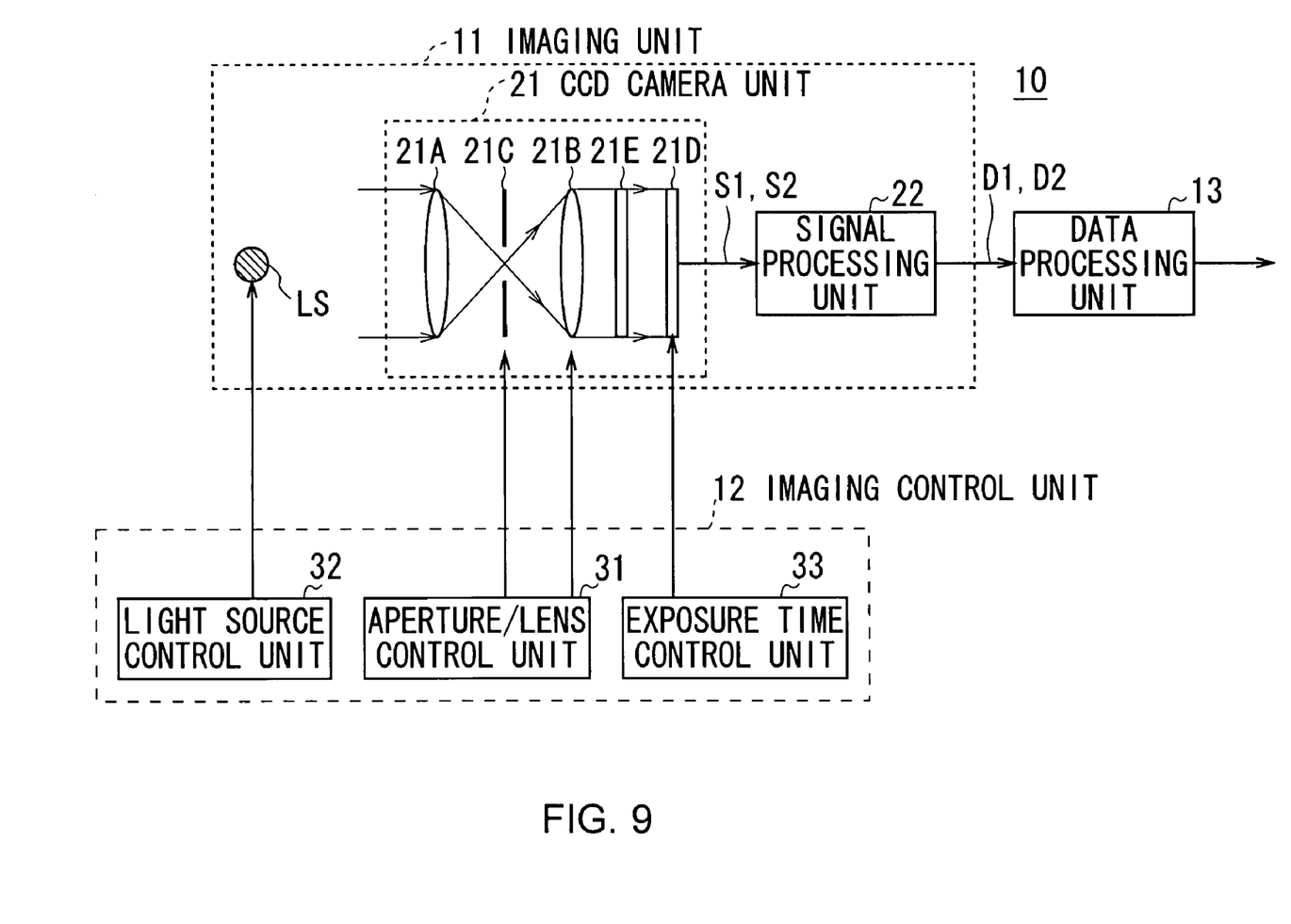
FIG. 9 is a schematic diagram showing a construction of an imaging apparatus according to the second embodiment.

As shown in FIG. 9 where the same reference numerals are applied to parts corresponding to those of FIG. 2, an imaging apparatus 20 is identical to the imaging apparatus 10 of the first embodiment, except for using a complementary color CCD 51D adopting the complementary checker color difference line sequential method.

Figure 10:
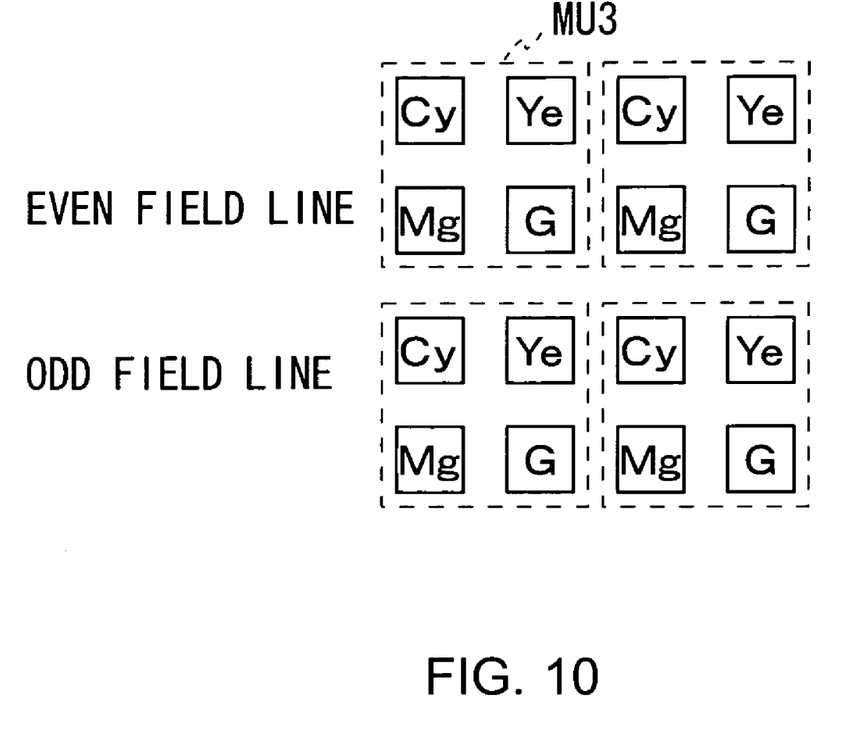
FIG. 10 is a schematic diagram showing a color filter array of a complementary color filter according to the second embodiment.

This complementary color CCD 51D has a most common color filter array in which four neighboring color pixels are arranged in a matrix as a unit for signal processing. Specifically, as shown in FIG. 10, the complementary color CCD 51D has a color filter array with color pixels "Cy", "Mg", "Ye", and "G" as a unit for signal processing MU3.

In actual, in a normal imaging mode, the imaging apparatus 20 (FIG. 9) adjusts the imaging conditions of relevant units of an imaging unit 11 under the control of an imaging control unit 12 according to this mode, and guides the outside light (visible light) in the air coming from a subject existing in front of a CCD camera unit 21, to the complementary color CCD 51D via a lens 21A, an aperture 21C and a lens 21B in order.

In a blood vessel imaging mode, on the other hand, the imaging apparatus 20 adjusts the imaging conditions of relevant units of the imaging unit 11 under the control of the imaging control unit 12 according to this mode, and guides blood vessel pattern light (near-infrared light) obtained via a body existing in front of the CCD camera unit 21, to the complementary color CCD 51D via the lens 21A, the aperture 21C and the lens 21B in order.

Then the complementary color CCD 51D performs the photoelectric conversion on the visible light or the blood vessel pattern light, and sequentially reads charge signals which have been stored in the photoelectric conversion elements as a result of this conversion, as composite signals from every two pixels in a column for every even or odd field line, as described with reference to FIG. 8, and sends these to a signal processing unit 22 as a subject image signal S11 or a blood vessel image signal S12.

The signal processing unit 22 performs a signal process under the complementary checker color difference line sequential method on the subject image signal S11 or the blood vessel image signal S12. Specifically, as shown in following equations:

$2n-1$ line luminance signal (1)

$$Y2n-1 = (Cy+MG)+(Ye+G), (Cy+Mg)+(Ye+G), \ldots$$
$$= Y(\approx 2R+3G+2B)$$

$2n+1$ line luminance signal $$Y2n+1 = (Cy+G)+(Ye+Mg), (Cy+G)+(Ye+Mg), \ldots$$
$$= Y(\approx 2R+3G+2B)$$

$2n-1$ line color difference signal $$C2n-1 = (Cy+MG)-(Ye+G), (Cy+Mg)-(Ye+G), \ldots$$
$$= Cb(\approx 2B-G)$$

$2n+1$ line color difference signal $$C2n+1 = (Cy+G)-(Ye+Mg), (Cy+G)-(Ye+Mg), \ldots$$
$$= -Cr(\approx -2R+G)$$

where Y is a luminance signal and Cb and Cy are color difference signals, the luminance signal Y is calculated by adding composite signals each from two neighboring pixels in a column or the color difference signals Cb and Cy are calculated by subtracting one composite signal from the other.

Then the signal processing unit 22 performs the A/D conversion on the result of the addition/subtraction process, and sends the resultant subject image data D11 or blood vessel image data D12 to the data processing unit 13.

As described above, the imaging apparatus 20 executes the normal imaging mode and the blood vessel imaging mode to image both normal subjects and blood vessel tissues existing inside a body, as imaging targets.

(2-2) Color Filter Characteristics of Complementary Color CCD

In this imaging apparatus 20, since the one complementary color CCD 51D performs the photoelectric conversion on both visible light and blood vessel pattern light (near-infrared light) arriving the CCD camera unit 21, a color purity is off balance due to near-infrared light components included in a result (subject image signal S11) of the photoelectric conversion of the complementary color CCD 51D in the normal imaging mode, resulting in deteriorating image quality of a subject image. This image quality deterioration becomes obvious because the complementary color CCD 51D suitable for emphasis of sensitivity and imaging more than color difference is applied.

Therefore, for the complementary color CCD 51D of this embodiment, color filter characteristics for each color pixel "Cy", "Mg", "Ye", "G" are selected so as not to disrupt a color purity balance due to near-infrared light components.

Specifically, the subject image signal S11 is sequentially read as composite signals output from every two pixels in a column for every even or odd field line, and the color difference signals Cb and Cy are calculated by subtracting a composite signal output from neighboring pixels from another composite signal in the signal processing unit 22 as shown in the equation (1). Therefore, if near-infrared light components included in the color difference signal Cb on an even field line and near-infrared light components included in the color difference signal Cy on an odd field line can be made equal to each other, the disruption of the color purity balance due to near-infrared light components can be avoided.

In this case, color space conversion between "Cy", "G", "Mg", "Ye" signals, and "R" or "B" signal is generally shown as follows:

$$R = 0.4Cy + 0.4G - 0.2 Ye - 0.4Mg$$

$$B = 0.6Cy + 0.4Mg - 0.4Ye - 0.2G \quad (2)$$

Figure 11:
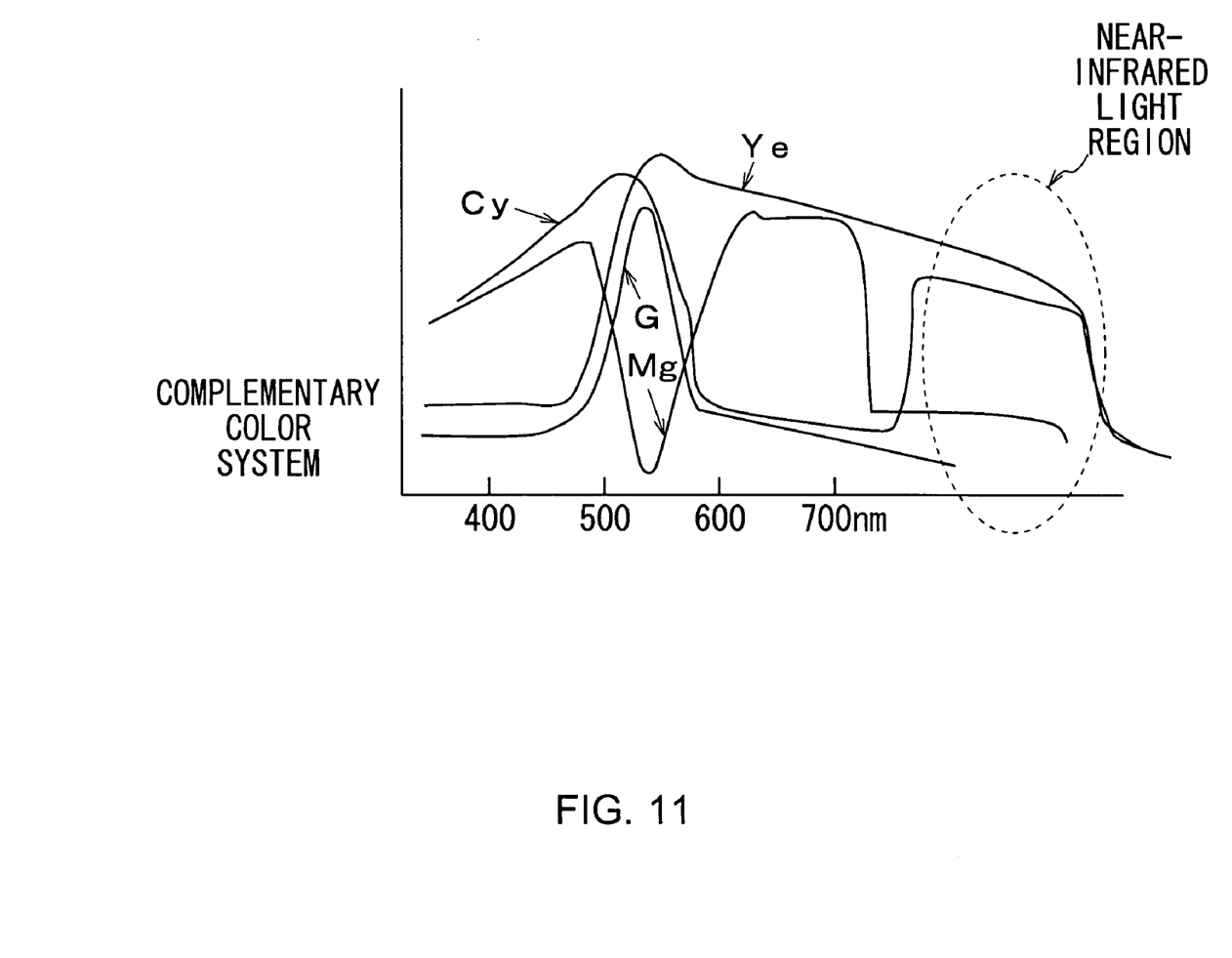
FIG. 11 is a schematic diagram showing filter characteristics.

Therefore, to take "N" components included in the color difference signals Cb and Cy as "0", "6":"1":"0":"10" may be selected as the near-infrared-light transparent ratio of "Cy" pixel, "G" pixel, "Mg" pixel, and "Ye" pixel of the complementary color CCD 51D. In this case, visual color filter characteristics of the complementary color CCD 51D are shown in FIG. 11. Note that the transparent ratio means a relative ratio, not a ratio of primary colors.

In actual, when the color difference signals Cb and Cy are calculated from the subject image signal S11 which is sequentially obtained via the complementary color CCD 51D at the transparent ratio, it can be known from the following equation that the "N" components are offset.

$$R = 0.4(Cy + 0.6N) + 0.4G - 0.2(Ye + N) - 0.4(Mg + 0.1N) \quad (3)$$
$$= 0.4Cy + 0.4G - 0.2 Ye - 0.4 Mg$$
$$B = 0.6(Cy + 0.6N) + 0.4(Mg + 0.1N) - 0.4(Ye + N) - 0.2G$$
$$= 0.6 Cy + 0.4Mg - 0.4Ye - 0.2 G$$

Therefore, a subject image can be obtained without disrupting a color purity.

When the luminance signal Y is calculated from the subject image signal S11, on the other hand, deterioration occurs due to the "N" components as indicated by the following equation.

$$(Cy+0.6N)+(Mg+0.1N)+G+(Ye+N)=Y+1.7N \quad (4)$$

This deterioration problem can be solved by combining a luminance signal created from lower components of the color signals Cb and Cy and the equation (4). In this connection, an optical system can be designed so as to reduce resolution for near-infrared light.

When the complementary color CCD 51D is adopted, a color difference signal cannot be obtained in the blood vessel imaging mode. This, however, does not affect the extraction of a blood vessel formation pattern of blood vessel tissues for imaging, and therefore is no problem.

(2-3) Operation and Effects of the Second Embodiment

According to the above configuration, in this imaging apparatus 20, the relative near-infrared-light transparent ratio of the color pixels of the complementary color CCD 51D in a unit for signal processing MU3 is selected so that the "N" components included in the color difference signals Cb and Cy after the color space conversion become "0".

Therefore, as in the first embodiment case, the imaging apparatus 20 can use one complementary color CCD 51D to image both imaging targets, resulting in realizing downsizing and eliminating complexity in manufacturing and usage, as compared with a case of providing special filters according to modes.

In addition, this imaging apparatus 20 can image both imaging targets without deteriorating image quality of a normal subject and blood vessel tissues existing inside a body with only one complementary color CCD 51D, thus being capable of significantly improving image quality as compared with the complementary color CCD shown in FIG. 10.

According to the above configuration, the relative near-infrared-light transparent ratio of the color pixels of the complementary color CCD 51D in the unit for signal processing MU3 is selected so that the "N" components included in the color difference signals Cb and Cy after the color space conversion become "0", so that the both imaging targets can be imaged with only one complementary color CCD 51D without deteriorating image quality of a normal subject and blood vessel tissues existing inside a body, thus being capable of improving usability as compared with the above described first embodiment.

(2-4) Other Configurations in the Second Embodiment

The above second embodiment has described a case of applying the complementary color CCD 51D (that is, integrated with a CCD) as a filter means for allowing visible light reflected by a subject and near-infrared light to pass therethrough. This invention, however, is not limited to this and a filter comprising a color filter array of the color CCD 51D can be provided separately from the CCD at a prescribed position on the light path.

Further, the above second embodiment has described a case of selecting a relative near-infrared-light transparent ratio of the color pixels of the complementary color CCD 51D in the unit for signal processing MU3 so that the "N" components included in the color difference signals Cb and Cy after the color space conversion of the equation (2) of the signal processing unit 22 become "0". This invention, however, is not limited to this and a different type of complementary color CCD can be used and the CCD can have the different number of color pixels as a unit for signal processing. In addition, the signal processing unit 22 can be a signal processing means for performing a signal process other than the color space conversion of the equation (2), and "N" components can be set to a prescribed value or later, not "0". In short, a complementary color CCD can have a color filter array with a plurality of color pixels for performing color dispersion on visible light as a unit, and a relative near-infrared-light transparent ratio of the color pixels can be selected so that the near-infrared light components included in a signal after a prescribed signal process become a prescribed value or lower.

Furthermore, the above second embodiment has described a case of using the complementary color CCD 51D as the solid imaging element. This invention, however, is not limited to this and a complementary Metal Oxide Semiconductor (CMOS) can be used instead.

In this case, differently from the CCD, the CMOS can easily obtain a pixel-independent signal by controlling horizontal scanning and/or vertical scanning, so that the same effects as the above embodiment can be obtained without limiting arrangement conditions.

(3) Other Configurations in First and Second Embodiments

The above embodiments have described a case where an irradiation means for irradiating a body with near-infrared light of a luminance level higher than that of visible light arriving the body controls an output value such as voltage to be output to the near-infrared light sources LS so as to be a prescribed set value as a luminance level higher than that of the outside light which is normally obtained in the air. This invention, however, is not limited to this and, for example, the luminance level of the outside light is detected, and the output value to be output to the near-infrared light sources LS can be controlled so as to become a set value determined according to the detection. By doing this, near-infrared light of a luminance level according to a situation where blood vessels are imaged can be emitted, resulting in being capable of reducing power consumption as compared with a case of always emitting near-infrared light of the same strength.

In addition, light including light of wavelength which has a specificity for the blood vessel tissues of both arteries and vein existing inside a body is emitted. This invention, however, is not limited to this and light including light of wavelength which has a specificity for the blood vessel tissues of one of the arteries and vein can be emitted.

In addition, in this case, a finger is applied as an irradiation target. This invention, however, is not limited to this and another part such as retina or all body can be applied.

Furthermore, the above embodiments have described a case where near-infrared light sources LS (LSa and LSb) are arranged at the almost same level as the CCD camera unit 21 and near-infrared light is emitted in a direction opposite to the entering direction to the color CCD 21D. This invention, however, is not limited to this and one or two or more near-infrared light sources can be arranged at different positions and near-infrared light can be emitted from the different directions.

Furthermore, the above embodiments have described a case where an exposure time adjustment means for adjusting exposure time of the solid imaging element does resetting at prescribed reset timing within the charge storage period t1 (FIG. 5A). This invention, however, is not limited to this and reset timing within the charge storage period t1 (FIG. 5A) can be changed according to one or both of the light amount adjustment of the aperture/lens control unit 31 and a set value in controlling output to the near-infrared light sources LS. By doing this, the imaging sensitivity of the color CCD 21D to the blood vessel pattern light can be adaptively adjusted, so that a blood vessel image signal S2 which faithfully represents the blood vessel tissues of a finger FG can be created.

This invention can be used for an electronic device for taking still images or moving images of a subject as an imaging target.

While there has been described in connection with the preferred embodiments of the invention, it will be obvious to those skilled in the art that various changes and modifications may be aimed, therefore, to cover in the appended claims all such changes and modifications as fall within the true spirit and scope of the invention.

What is claimed is:

1. An imaging apparatus configured to operate in a first mode to image a subject as an imaging target and in a second mode to image an inside of a body as the imaging target, comprising:
   irradiation means for irradiating the body with near-infrared light of a prescribed luminance level;
   filter means comprising a color filter array including a plurality of units for signal processing, each of the plurality of units including a group of neighboring pixels that include prescribed color pixels for performing color dispersion on visible light reflected by the subject and a near-infrared light pixel for allowing the near-infrared light to pass therethrough; and
   exposure time adjustment means for adjusting an exposure time of a solid imaging element for performing the color dispersion and photoelectric conversion on a pattern of the near-infrared light and the visible light reflected by the subject, wherein
   the exposure time adjustment means adjusts the exposure time of the solid imaging element based on the operation mode of the imaging apparatus.

2. The imaging apparatus according to claim 1, wherein the near-infrared light pixel allows the near-infrared light including light of a wavelength which has a specificity for blood vessel tissues of both arteries and vein existing inside the body, to pass therethrough.

3. The imaging apparatus according to claim 1, wherein the filter means is included in the solid imaging element and captures the imaging target.

4. The imaging apparatus according to claim 1, wherein the exposure time adjustment means sets a shorter exposure time when the imaging apparatus operates in the second mode than when the imaging apparatus operates in the first mode.

5. The imaging apparatus according to claim 1, wherein each of the plurality of units includes the group of neighboring pixels that are arranged in a matrix.

6. An imaging apparatus configured to operate in a first mode to image a subject as an imaging target and in a second mode to image an inside of a body as the imaging target, comprising:
   irradiation means for irradiating the body with near-infrared light of a prescribed luminance level;
   filter means for allowing visible light reflected by the subject and the near-infrared light to pass therethrough;
   exposure time adjustment means for adjusting an exposure time of a solid imaging element for performing photoelectric conversion on the visible light and the near-infrared light; and
   signal processing means for performing a signal process on a result of the photoelectric conversion of the solid imaging element, wherein
   the filter means comprises a color filter array with a plurality of color pixels for performing color dispersion on the visible light as a unit and selects a relative near-infrared-light transparent ratio of the plurality of color pixels so that near-infrared light components included in a signal after the signal process become a prescribed value or lower.

7. The imaging apparatus according to claim 6, wherein the filter means comprises a color filter array with complementary color pixels as a unit and selects the relative near-infrared-light transparent ratio of the plurality of color pixels so that near-infrared light components included in a signal after a prescribed color space conversion become a prescribed value or lower.

8. The imaging apparatus according to claim 6, wherein the filter means is included in the solid imaging element and captures the imaging target.

9. The imaging apparatus according to claim 6, wherein the filter means selects a different relative near-infrared-light transparent ratio for each of the plurality of color pixels so that near-infrared light components included in the signal after the prescribed color space conversion become the prescribed value or lower.

10. An imaging apparatus configured to operate in a first mode to image a subject as an imaging target and in a second mode to image an inside of a body as the imaging target, comprising:
   a light source configured to irradiate the body with near-infrared light of a prescribed luminance level;
   a filter unit comprising a color filter array including a plurality of units for signal processing, each of the plurality of units including a group of neighboring pixels that include prescribed color pixels configured to perform color dispersion on visible light reflected by the subject and a near-infrared light pixel configured to allow the near-infrared light to pass therethrough as a unit; and
   an exposure time adjustment unit configured to adjust an exposure time of a solid imaging element that is configured to perform the color dispersion and photoelectric conversion on a pattern of the near-infrared light and the useable light reflected by the subject, wherein the exposure time adjustment unit is configured to adjust the exposure time of the solid imaging element based on the operation mode of the imaging apparatus.

11. The imaging apparatus according to claim 10, wherein the filter unit is included in the solid imaging element and is configured to capture the imaging target.

12. The imaging apparatus according to claim 10, wherein the exposure time adjustment unit is configured to set a shorter exposure time when the imaging apparatus operates in the second mode than when the imaging apparatus operates in the first mode.

13. The imaging apparatus according to claim 10, wherein each of the plurality of units includes the group of neighboring pixels that are arranged in a matrix.

14. An imaging apparatus configured to operate in a first mode to image a subject as an imaging target and in a second mode to image an inside of a body as the imaging target, comprising:
   a light source configured to irradiate the body with near-infrared light of a prescribed luminance level;
   a filter unit configured to allow visible light reflected by the subject and the near-infrared light to pass therethrough;
   an exposure time adjustment unit configured to adjust an exposure time of a solid imaging element configured to perform a photoelectric conversion on the visible light and the near-infrared light; and
   a signal processing unit configured to perform a signal process on a result of the photoelectric conversion of the solid imaging element, wherein
   the filter unit comprises a color filter array with a plurality of color pixels configured to perform color dispersion on the visible light as a unit and is configured to select a relative near-infrared-light transparent ratio of the plurality of color pixels so that near-infrared light components included in a signal after the signal process become a prescribed value or lower.

15. The imaging apparatus according to claim 14, wherein the filter unit is included in the solid imaging element and is configured to capture the imaging target.

16. The imaging apparatus according to claim 14, wherein the filter unit is configured to select a different relative near-infrared-light transparent ratio for each of the plurality of color pixels so that near-infrared light components included in the signal after the signal process become the prescribed value or lower.

* * * * *